US008617836B2

(12) United States Patent
Boender et al.

(10) Patent No.: US 8,617,836 B2
(45) Date of Patent: Dec. 31, 2013

(54) METHOD FOR PREDICTING THE RESPONSE OF LOCALLY ADVANCED RECTAL CANCER TO CHEMORADIOTHERAPY

(75) Inventors: Pieter Jacob Boender, Nijmegen (NL); Richard De Wijn, Nijmegen (NL); Anne Hansen Ree, Haslum (NO); Sigurd Folkvord, Oslo (NO); Kjersti Flatmark, Oslo (NO); Robby Ruijtenbeek, Utrecht (NL)

(73) Assignees: PamGene B.V., 'S-Hertogenbosch (NL); Oslo University Hospital, Oslo (NO)

( * ) Notice: Subject to any disclaimer, the term of this patent is extended or adjusted under 35 U.S.C. 154(b) by 263 days.

(21) Appl. No.: 13/138,848

(22) PCT Filed: Apr. 12, 2010

(86) PCT No.: PCT/EP2010/054769
§ 371 (c)(1),
(2), (4) Date: Nov. 7, 2011

(87) PCT Pub. No.: WO2010/116001
PCT Pub. Date: Oct. 14, 2010

(65) Prior Publication Data
US 2012/0135888 A1    May 31, 2012

(30) Foreign Application Priority Data

Apr. 10, 2009  (EP) .................................... 09157818
Apr. 10, 2009  (WO) ................ PCT/EP2009/054359

(51) Int. Cl.
*C12Q 1/48*    (2006.01)

(52) U.S. Cl.
USPC .............................................. 435/15; 506/11

(58) Field of Classification Search
None
See application file for complete search history.

(56) References Cited

U.S. PATENT DOCUMENTS

2007/0099250 A1   5/2007  Hu et al.
2010/0120055 A1   5/2010  Hornbeck et al.

FOREIGN PATENT DOCUMENTS

WO    WO 2008/054597 A2    5/2008

OTHER PUBLICATIONS

Versele et al., Response prediction to a multitargeted kinase inhibitor in cancer cell lines and xenograft tumors using high-content tyrosine peptide arrays with a kinetic readout, 2009, Molecular Cancer Therapeutics 8(7): 1846-1855.*
PCT Notification of Transmittal of the International Search Report and the Written Opinion of the International Searching Authority, or the Declaration issued by the European Patent Office in connection with PCT International Patent Application No. PCT/EP2010/054769, 16 pages, Oct. 22, 2010.
PCT Notification of Transmittal of the International Preliminary Report dated Apr. 7, 2011 from the European Patent Office in connection with PCT International Patent Application No. PCT/EP2010/054769, 9 pages.
PCT Notification Concerning Informal Communications with the Applicant dated Apr. 7, 2011 from the European Patent Office in connection with PCT International Patent Application No. PCT/EP2010/054769, 3 pages.
Folkvord S et al., entitled "Locally advanced rectal cancer (LARC)-prediction of response to preoperative chemoradiotherapy (CRT) by kinase activity profiling of pre-CRT tumor biopsies," Proceedings of the American Association for Cancer Research, vol. 49, Apr. 2008, p. 858.
Folkvord S et al., entitled "Prediction of Response to Preoperative Chemoradiotherapy in Rectal Cancer by Multiplex Kinase Activity Profiling," Int. J. Radiation Oncology-Biology-Physics, vol. 78, No. 2, 2010, 555-562.
Ruijtenbeek R et al., entitled "Kinase activity profiling in tumor tissues by PamChip peptide microarrays," Seminar/Workshop by Pamgene in conjunction with the Laboratory for Innovative Translational Technologies (LITT), Harvard School of Dental Medicine, Dec. 11, 2007, Abstract, 1 page.

* cited by examiner

*Primary Examiner* — Jon P Weber
*Assistant Examiner* — Robert Yamasaki
(74) *Attorney, Agent, or Firm* — Amster, Rothstein & Ebenstein LLP

(57) ABSTRACT

The present invention relates to a method for determining or predicting the response of a patient diagnosed with locally advanced rectal cancer to chemoradiotherapy. The present invention also aims to provide methods and devices for predicting the response of patients diagnosed with rectal cancer to specific medicaments, radiotherapy and/or chemotherapy. More specifically, the present invention provides methods which measure kinase activity by studying phosphorylation levels and profiles in samples of said patients.

12 Claims, 1 Drawing Sheet

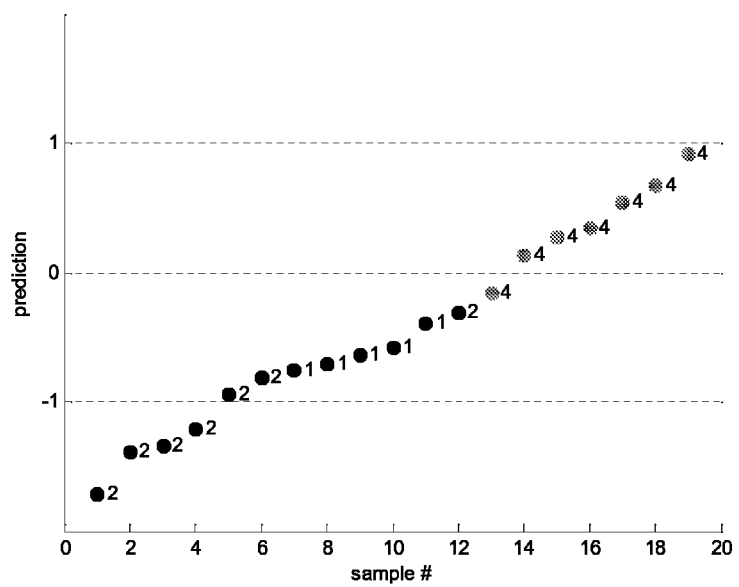

SEQUENCE LISTING

<160> NUMBER OF SEQ ID NOS: 86

<210> SEQ ID NO 1
<211> LENGTH: 13
<212> TYPE: PRT
<213> ORGANISM: Artificial Sequence
<220> FEATURE:
<223> OTHER INFORMATION: Peptide PGFRB_572_584

<400> SEQUENCE: 1

Val Ser Ser Asp Gly His Glu Tyr Ile Tyr Val Asp Pro
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Peptide EGFR_1165_1177

<400> SEQUENCE: 2

Ile Ser Leu Asp Asn Pro Asp Tyr Gln Gln Asp Phe Phe
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Peptide PGFRB_1014_1028

<400> SEQUENCE: 3

Pro Asn Glu Gly Asp Asn Asp Tyr Ile Ile Pro Leu Pro Asp Pro
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Peptide MK07_211_223

<400> SEQUENCE: 4

Ala Glu His Gln Tyr Phe Met Thr Glu Tyr Val Ala Thr

```
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Peptide LAT_249_261

<400> SEQUENCE: 5

Glu Glu Gly Ala Pro Asp Tyr Glu Asn Leu Gln Glu Leu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Peptide ERBB4_1277_1289

<400> SEQUENCE: 6

Ile Val Ala Glu Asn Pro Glu Tyr Leu Ser Glu Phe Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide EPHB1_771_783

<400> SEQUENCE: 7

Asp Asp Thr Ser Asp Pro Thr Tyr Thr Ser Ser Leu Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Peptide EPHA1_774_786

<400> SEQUENCE: 8

Leu Asp Asp Phe Asp Gly Thr Tyr Glu Thr Gln Gly Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide EPHA7_607_619

<400> SEQUENCE: 9

Thr Tyr Ile Asp Pro Glu Thr Tyr Glu Asp Pro Asn Arg
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide K2C6B_53_65

<400> SEQUENCE: 10

Gly Ala Gly Phe Gly Ser Arg Ser Leu Tyr Gly Leu Gly
1               5                   10
```

```
<210> SEQ ID NO 11
<211> LENGTH: 13
<212> TYPE: PRT
<213> ORGANISM: Artificial Sequence
<220> FEATURE:
<223> OTHER INFORMATION: Peptide P85A_600_612

<400> SEQUENCE: 11

Asn Glu Asn Thr Glu Asp Gln Tyr Ser Leu Val Glu Asp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide EPOR_419_431

<400> SEQUENCE: 12

Ala Ser Ala Ala Ser Phe Glu Tyr Thr Ile Leu Asp Pro
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Peptide FGFR2_762_774

<400> SEQUENCE: 13

Thr Leu Thr Thr Asn Glu Glu Tyr Leu Asp Leu Ser Gln
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Peptide PAXI_24_36

<400> SEQUENCE: 14

Phe Leu Ser Glu Glu Thr Pro Tyr Ser Tyr Pro Thr Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Peptide ANXA1_14_26

<400> SEQUENCE: 15

Ile Glu Asn Glu Glu Gln Glu Tyr Val Gln Thr Val Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Peptide FAK2_572_584

<400> SEQUENCE: 16

Arg Tyr Ile Glu Asp Glu Asp Tyr Tyr Lys Ala Ser Val
1               5                   10

<210> SEQ ID NO 17
```

-continued

```
<211> LENGTH: 13
<212> TYPE: PRT
<213> ORGANISM: Artificial Sequence
<220> FEATURE:
<223> OTHER INFORMATION: Peptide ERBB2_870_882

<400> SEQUENCE: 17

Leu Asp Ile Asp Glu Thr Glu Tyr His Ala Asp Gly Gly
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Peptide SRC8_CHICK_474_488

<400> SEQUENCE: 18

Glu Tyr Glu Pro Glu Thr Val Tyr Glu Val Ala Gly Ala
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Peptide EPHA2_765_777

<400> SEQUENCE: 19

Glu Asp Asp Pro Glu Ala Thr Tyr Thr Thr Ser Gly Gly
1               5                   10

<210> SEQ ID NO 20
<211> LENGTH: 13
<212> TYPE: PRT
<213> ORGANISM: Artificial Sequence
<220> FEATURE:
<223> OTHER INFORMATION: PAXI_111_123

<400> SEQUENCE: 20

Val Gly Glu Glu Glu His Val Tyr Ser Phe Pro Asn Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Peptide Abl_artificial_kinase_substrate

<400> SEQUENCE: 21

Glu Ala Ile Tyr Ala Ala Pro Phe Ala Lys Lys Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Peptide TNNT1_2_14

<400> SEQUENCE: 22

Ser Asp Thr Glu Glu Gln Glu Tyr Glu Glu Glu Gln Pro
1               5                   10

<210> SEQ ID NO 23
<211> LENGTH: 13
<212> TYPE: PRT
```

```
<213> ORGANISM: Artificial Sequence
<220> FEATURE:
<223> OTHER INFORMATION: Peptide CBL_693_705

<400> SEQUENCE: 23

Glu Gly Glu Glu Asp Thr Glu Tyr Met Thr Pro Ser Ser
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Peptide CDK2_8_20

<400> SEQUENCE: 24

Glu Lys Ile Gly Glu Gly Thr Tyr Gly Val Val Tyr Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Peptide JAK1_1015_1027

<400> SEQUENCE: 25

Ala Ile Glu Thr Asp Lys Glu Tyr Tyr Thr Val Lys Asp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Peptide INSR_992_1004

<400> SEQUENCE: 26

Tyr Ala Ser Ser Asn Pro Glu Tyr Leu Ser Ala Ser Asp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Peptide LAT_194_206

<400> SEQUENCE: 27

Met Glu Ser Ile Asp Asp Tyr Val Asn Val Pro Glu Ser
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Peptide EGFR_1103_1115

<400> SEQUENCE: 28

Gly Ser Val Gln Asn Pro Val Tyr His Asn Gln Pro Leu
1               5                   10

<210> SEQ ID NO 29
<211> LENGTH: 13
<212> TYPE: PRT
<213> ORGANISM: Artificial Sequence
<220> FEATURE:
```

```
<223> OTHER INFORMATION: Peptide CTNB1_79_91

<400> SEQUENCE: 29

Val Ala Asp Ile Asp Gly Gln Tyr Ala Met Thr Arg Ala
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Peptide PDPK1_369_381

<400> SEQUENCE: 30

Asp Glu Asp Cys Tyr Gly Asn Tyr Asp Asn Leu Leu Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Peptide ERBB2_1241_1253

<400> SEQUENCE: 31

Pro Thr Ala Glu Asn Pro Glu Tyr Leu Gly Leu Asp Val
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Peptide 41_654_666

<400> SEQUENCE: 32

Leu Asp Gly Glu Asn Ile Tyr Ile Arg His Ser Asn Leu
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Peptide EPOR_361_373

<400> SEQUENCE: 33

Ser Glu His Ala Gln Asp Thr Tyr Leu Val Leu Asp Lys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Peptide FER_707_719

<400> SEQUENCE: 34

Arg Gln Glu Asp Gly Gly Val Tyr Ser Ser Ser Gly Leu
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Peptide RET_1022_1034
```

```
<400> SEQUENCE: 35

Thr Pro Ser Asp Ser Leu Ile Tyr Asp Asp Gly Leu Ser
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Peptide FES_706_718

<400> SEQUENCE: 36

Arg Glu Glu Ala Asp Gly Val Tyr Ala Ala Ser Gly Gly
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Peptide VGFR2_1052_1064

<400> SEQUENCE: 37

Asp Ile Tyr Lys Asp Pro Asp Tyr Val Arg Lys Gly Asp
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Peptide SRC8_CHICK_470_482

<400> SEQUENCE: 38

Val Ser Gln Arg Glu Ala Glu Tyr Glu Pro Glu Thr Val
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Peptide PDPK1_2_14

<400> SEQUENCE: 39

Ala Arg Thr Thr Ser Gln Leu Tyr Asp Ala Val Pro Ile
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Peptide JAK2_563_577

<400> SEQUENCE: 40

Val Arg Arg Glu Val Gly Asp Tyr Gly Gln Leu His Glu Thr Glu
1               5                   10                  15

<210> SEQ ID NO 41
<211> LENGTH: 13
<212> TYPE: PRT
<213> ORGANISM: Artificial Sequence
<220> FEATURE:
<223> OTHER INFORMATION: Peptide PECA1_706_718

<400> SEQUENCE: 41
```

```
Lys Lys Asp Thr Glu Thr Val Tyr Ser Glu Val Arg Lys
1               5                   10
```

<210> SEQ ID NO 42
<211> LENGTH: 13
<212> TYPE: PRT
<213> ORGANISM: Artificial Sequence
<220> FEATURE:
<223> OTHER INFORMATION: Peptide MBP_198_210

<400> SEQUENCE: 42

```
Ala Arg Thr Ala His Tyr Gly Ser Leu Pro Gln Lys Ser
1               5                   10
```

<210> SEQ ID NO 43
<211> LENGTH: 13
<212> TYPE: PRT
<213> ORGANISM: Artificial Sequence
<220> FEATURE:
<223> OTHER INFORMATION: Peptide VGFR2_989_1001

<400> SEQUENCE: 43

```
Glu Glu Ala Pro Glu Asp Leu Tyr Lys Asp Phe Leu Thr
1               5                   10
```

<210> SEQ ID NO 44
<211> LENGTH: 13
<212> TYPE: PRT
<213> ORGANISM: Artificial Sequence
<220> FEATURE:
<223> OTHER INFORMATION: Peptide NTRK2_696_708

<400> SEQUENCE: 44

```
Gly Met Ser Arg Asp Val Tyr Ser Thr Asp Tyr Tyr Arg
1               5                   10
```

<210> SEQ ID NO 45
<211> LENGTH: 13
<212> TYPE: PRT
<213> ORGANISM: Artificial Sequence
<220> FEATURE:
<223> OTHER INFORMATION: Peptide MET_1227_1239

<400> SEQUENCE: 45

```
Arg Asp Met Tyr Asp Lys Glu Tyr Tyr Ser Val His Asn
1               5                   10
```

<210> SEQ ID NO 46
<211> LENGTH: 13
<212> TYPE: PRT
<213> ORGANISM: Artificial Sequence
<220> FEATURE:
<223> OTHER INFORMATION: Peptide ACHD_383_395

<400> SEQUENCE: 46

```
Tyr Ile Ser Lys Ala Glu Glu Tyr Phe Leu Leu Lys Ser
1               5                   10
```

<210> SEQ ID NO 47
<211> LENGTH: 13
<212> TYPE: PRT
<213> ORGANISM: Artificial Sequence
<220> FEATURE:
<223> OTHER INFORMATION: Peptide PRGR_786_798

<400> SEQUENCE: 47

```
Glu Gln Arg Met Lys Glu Ser Ser Phe Tyr Ser Leu Cys
1               5                   10
```

```
<210> SEQ ID NO 48
<211> LENGTH: 13
<212> TYPE: PRT
<213> ORGANISM: Artificial Sequence
<220> FEATURE:
<223> OTHER INFORMATION: Peptide CD3Z_116_128

<400> SEQUENCE: 48

Lys Asp Lys Met Ala Glu Ala Tyr Ser Glu Ile Gly Met
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Peptide PLCG1_764_776

<400> SEQUENCE: 49

Ile Gly Thr Ala Glu Pro Asp Tyr Gly Ala Leu Tyr Glu
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Peptide RASA1_453_465

<400> SEQUENCE: 50

Thr Val Asp Gly Lys Glu Ile Tyr Asn Thr Ile Arg Arg
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Peptide PGFRB_768_780

<400> SEQUENCE: 51

Ser Ser Asn Tyr Met Ala Pro Tyr Asp Asn Tyr Val Pro
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Peptide FRK_380_392

<400> SEQUENCE: 52

Lys Val Asp Asn Glu Asp Ile Tyr Glu Ser Arg His Glu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Peptide DYR1A_312_324

<400> SEQUENCE: 53

Cys Gln Leu Gly Gln Arg Ile Tyr Gln Tyr Ile Gln Ser
1               5                   10
```

<210> SEQ ID NO 54
<211> LENGTH: 13
<212> TYPE: PRT
<213> ORGANISM: Artificial Sequence
<220> FEATURE:
<223> OTHER INFORMATION: Peptide PGFRB_771_783

<400> SEQUENCE: 54

Tyr Met Ala Pro Tyr Asp Asn Tyr Val Pro Ser Ala Pro
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Peptide FAK1_569_581

<400> SEQUENCE: 55

Arg Tyr Met Glu Asp Ser Thr Tyr Tyr Lys Ala Ser Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Peptide DCX_109_121

<400> SEQUENCE: 56

Gly Ile Val Tyr Ala Val Ser Ser Asp Arg Phe Arg Ser
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Peptide PGFRB_709_721

<400> SEQUENCE: 57

Arg Pro Pro Ser Ala Glu Leu Tyr Ser Asn Ala Leu Pro
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Peptide TEC_512_524

<400> SEQUENCE: 58

Arg Tyr Phe Leu Asp Asp Gln Tyr Thr Ser Ser Ser Gly
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Peptide VGFR2_1168_1180

<400> SEQUENCE: 59

Ala Gln Gln Asp Gly Lys Asp Tyr Ile Val Leu Pro Ile
1               5                   10

<210> SEQ ID NO 60
<211> LENGTH: 13

```
<212> TYPE: PRT
<213> ORGANISM: Artificial Sequence
<220> FEATURE:
<223> OTHER INFORMATION: Peptide MK12_178_190

<400> SEQUENCE: 60

Ala Asp Ser Glu Met Thr Gly Tyr Val Val Thr Arg Trp
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Peptide FGFR3_753_765

<400> SEQUENCE: 61

Thr Val Thr Ser Thr Asp Glu Tyr Leu Asp Leu Ser Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Peptide PRRX2_202_214

<400> SEQUENCE: 62

Trp Thr Ala Ser Ser Pro Tyr Ser Thr Val Pro Pro Tyr
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Peptide SRC8_CHICK_492_504

<400> SEQUENCE: 63

Tyr Gln Ala Glu Glu Asn Thr Tyr Asp Glu Tyr Glu Asn
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Peptide VGFR1_1326_1338

<400> SEQUENCE: 64

Asp Tyr Asn Ser Val Val Leu Tyr Ser Thr Pro Pro Ile
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Peptide ZAP70_485_497

<400> SEQUENCE: 65

Ala Leu Gly Ala Asp Asp Ser Tyr Tyr Thr Ala Arg Ser
1               5                   10

<210> SEQ ID NO 66
<211> LENGTH: 13
<212> TYPE: PRT
<213> ORGANISM: Artificial Sequence
```

```
<220> FEATURE:
<223> OTHER INFORMATION: Peptide ODBA_340_352

<400> SEQUENCE: 66

Asp Asp Ser Ser Ala Tyr Arg Ser Val Asp Glu Val Asn
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Peptide FGFR1_761_773

<400> SEQUENCE: 67

Thr Ser Asn Gln Glu Tyr Leu Asp Leu Ser Met Pro Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Peptide PP2AB_297_309

<400> SEQUENCE: 68

Glu Pro His Val Thr Arg Arg Thr Pro Asp Tyr Phe Leu
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Peptide RAF1_332_344

<400> SEQUENCE: 69

Pro Arg Gly Gln Arg Asp Ser Ser Tyr Tyr Trp Glu Ile
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Peptide MK10_216_228

<400> SEQUENCE: 70

Thr Ser Phe Met Met Thr Pro Tyr Val Val Thr Arg Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Peptide AMPE_5_17

<400> SEQUENCE: 71

Glu Arg Glu Gly Ser Lys Arg Tyr Cys Ile Gln Thr Lys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Peptide PGFRB_1002_1014
```

```
<400> SEQUENCE: 72

Leu Asp Thr Ser Ser Val Leu Tyr Thr Ala Val Gln Pro
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Peptide RON_1346_1358

<400> SEQUENCE: 73

Ser Ala Leu Leu Gly Asp His Tyr Val Gln Leu Pro Ala
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Peptide CDK7_157_169

<400> SEQUENCE: 74

Gly Leu Ala Lys Ser Phe Gly Ser Pro Asn Arg Ala Tyr
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Peptide MK01_180_192

<400> SEQUENCE: 75

His Thr Gly Phe Leu Thr Glu Tyr Val Ala Thr Arg Trp
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Peptide RB_804_816

<400> SEQUENCE: 76

Ile Tyr Ile Ser Pro Leu Lys Ser Pro Tyr Lys Ile Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Peptide VINC_815_827

<400> SEQUENCE: 77

Lys Ser Phe Leu Asp Ser Gly Tyr Arg Ile Leu Gly Ala
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Peptide MBP_259_271

<400> SEQUENCE: 78
```

Phe Gly Tyr Gly Gly Arg Ala Ser Asp Tyr Lys Ser Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Peptide PYN11_539_551

<400> SEQUENCE: 79

Ser Lys Arg Lys Gly His Glu Tyr Thr Asn Ile Lys Tyr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Peptide CALM_95_107

<400> SEQUENCE: 80

Lys Asp Gly Asn Gly Tyr Ile Ser Ala Ala Glu Leu Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Peptide TYRO3_679_691

<400> SEQUENCE: 81

Lys Ile Tyr Ser Gly Asp Tyr Tyr Arg Gln Gly Cys Ala
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Peptide ZBT16_621_633

<400> SEQUENCE: 82

Leu Arg Thr His Asn Gly Ala Ser Pro Tyr Gln Cys Thr
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Peptide MBP_263_275

<400> SEQUENCE: 83

Gly Arg Ala Ser Asp Tyr Lys Ser Ala His Lys Gly Phe
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Peptide NCF1_313_325

<400> SEQUENCE: 84

Gln Arg Ser Arg Lys Arg Leu Ser Gln Asp Ala Tyr Arg

-continued

```
<210> SEQ ID NO 85
<211> LENGTH: 13
<212> TYPE: PRT
<213> ORGANISM: Artificial Sequence
<220> FEATURE:
<223> OTHER INFORMATION: Peptide NPT2A_501_513

<400> SEQUENCE: 85

Ala Lys Ala Leu Gly Lys Arg Thr Ala Lys Tyr Arg Trp
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Peptide VGFR2_944_956

<400> SEQUENCE: 86

Arg Phe Arg Gln Gly Lys Asp Tyr Val Gly Ala Ile Pro
1               5                   10
```

METHOD FOR PREDICTING THE RESPONSE OF LOCALLY ADVANCED RECTAL CANCER TO CHEMORADIOTHERAPY

CROSS-REFERENCE TO RELATED APPLICATIONS

This application is a U.S. national stage entry under 35 U.S.C. §371 of PCT International Patent Application No. PCT/EP2010/054769, filed Apr. 12, 2010, and claims priority to European Patent Application No. 09157818.7, filed Apr. 10, 2009 and PCT International Patent Application No. PCT/EP2009/054359, filed Apr. 10, 2009, the contents of which are incorporated herein by reference in their entirety.

FIELD OF THE INVENTION

The present invention relates to a method for determining or predicting the response of a patient diagnosed with locally advanced rectal cancer to chemoradiotherapy. The present invention also aims to provide methods and devices for predicting the response of patients diagnosed with rectal cancer to specific treatments. More specifically, the present invention provides methods which measure kinase activity by studying phosphorylation levels and profiles in samples of said patients.

BACKGROUND OF THE INVENTION

Colorectal cancer is a major public health problem in the Western world and ranks as the third leading cause of death in both males and females. In 2000, more than 9000 new colorectal cancer patients were registered in the Netherlands, of whom 25% had rectal cancer. Rectal cancer is a disease in which malignant (cancer) cells form in the tissues of the rectum.

The term locally advanced rectal cancer (LARC) encompasses rectal tumors that by clinical or radiological assessment grow through the rectal wall to an extent that complete removal by surgery alone is considered impossible. Using TNM classification, a cancer staging system for the classification of malignant tumours, the extent of cancer in a patient's body is described. LARC is typically staged as a T3 or T4 tumor, and involves the mesorectal compartment or infiltrates adjacent pelvic structures respectively.

Relapses from rectal cancer following primary treatment occur as local recurrences or distant metastases, mainly to liver or lungs. Local recurrences arise if primary treatment has not resulted in local control, whereas distant metastases develop because of dissemination of tumor cells by lymphatic or blood circulation.

A major problem in LARC is the thread of local recurrence, not only because of the limited therapeutic options but especially because of the impaired quality of life due to the intense pain and uncontrolled soiling. There are therefore four major goals in the treatment of a patient with rectal cancer: (1) local control; (2) long-term survival; (3) preservation of anal sphincter, bladder, and sexual function; and (4) maintenance or improvement in quality of life.

Randomized trials have shown that the best local control rate for rectal cancer patients is achieved after a short course of radiation and chemotherapy followed by optimal surgery. The addition of this preoperative chemoradiotherapy has changed the treatment of LARC dramatically as shown in several trials showing improvements over traditional removal of the tumor without preoperative treatment. Thus the standard treatment of LARC is multimodal, involving preoperative chemoradiotherapy aimed at down-staging the tumor to allow subsequent complete surgical removal or resection. The chemotherapy component of this therapeutic strategy is intended to sensitize the tumor to ionizing radiation. However, radiation therapy also causes damage to healthy tissues, which confers the risk of short- and long-term complications.

An important factor when performing radiation treatment is that the response to chemoradiotherapy varies greatly, from complete response with no remaining tumor tissue, observed in 0-30% of patients, to no objective response. Hence, it would be useful to select and treat only those patients likely to benefit from preoperative chemoradiotherapy. The identified non-responders are at that point candidates for other treatments like alternative radiosensitizing regimens.

At present no clinical or analytical tools are available to make the distinction between responders and non-responders prior to deciding which treatment to administer although a few attempts of predictive biomarkers have been described in the literature such as Smac expression (assessed by immunohistochemistry), epidermal growth factor receptor expression (assessed by immunohistochemistry) and c-K-ras gene mutations. These methods are however highly variable, not robust and show poor predictivity since these screenings are based on the detection of a limited number of proteins or genes and a small variation in the gene or protein expression will have profound effects on the screening method.

In view of the above, there remains a pressing need for methods that provide a fast and accurate prediction of the response of a patient diagnosed with rectal cancer to induction chemoradiotherapy. These methods would enable to provide information regarding the efficacy of the preoperative chemoradiotherapy treatment, and more specifically provide an early determination of the most suited treatment of the rectal cancer patient.

The present invention aims at providing methods and devices for predicting the response of a patient diagnosed with rectal cancer to induction chemoradiotherapy. The present invention also aims to provide methods and devices for predicting the response of patients diagnosed with rectal cancer to specific medicaments, radiotherapy and/or chemotherapy treatments. The method of the present invention therefore adds to the existing assays currently used to select therapies in rectal cancer patients.

SUMMARY OF THE INVENTION

The present invention provides methods and devices that enable the determination of the response of a patient diagnosed with rectal cancer to (induction) chemoradiotherapy by measuring kinase activity of a rectal cancer sample. The present invention further shows how the method and devices can be used to predict the response of patients diagnosed with rectal cancer to specific treatments. The method of the present invention therefore adds to the existing assays currently used to select therapies in rectal cancer patients.

The present invention therefore provides a method for determining or predicting the response of a patient diagnosed with rectal cancer to (induction) chemoradiotherapy. In a first embodiment of the present invention, the method comprises the steps of:

(a) measuring kinase activity of a sample, obtained from the rectal cancer tumor from said patient, thereby providing a phosphorylation profile of said sample, said phosphorylation profile comprising the phosphorylation levels of phosphorylation sites present in at least two peptide markers as listed in Table 1; and, (b) determining from said phosphorylation profile the response of said patient to chemoradiotherapy.

In another embodiment, the present invention regards the method according to the present invention wherein said peptide markers are any of the peptide markers selected from the group consisting of the peptide markers with any of SEQ ID NO 1 to 21.

According to a particular embodiment, the present invention regards the method according to the present invention wherein said peptide markers are any of the peptide markers selected from the group consisting of the peptide markers with any of SEQ ID NO 1, 2, 3, 4, 5, 6, 7, 21, 32, 42, 51, 54, 61, 62, 63, 67, 71, 74, 79, 80, 81, 82, 83, 85, and 86.

In a further embodiment, the present invention relates to a method according to the present invention wherein said chemoradiotherapy is a preoperative neoadjuvant chemoradiotherapy. A preoperative neoadjuvant therapy is a therapy consisting of chemotherapy and radiotherapy. Such as radiotherapy of 50 Gy in 2-Gy fractions 5 days per week for a period of 5 weeks and chemotherapy consisting of capecitabine: twice daily on radiotherapy days and oxaliplatin once weekly.

Another embodiment of the present invention relates to a method for predicting the response of a patient, diagnosed with rectal cancer, to a medicament, radiotherapy and/or chemotherapy, wherein the kinase activity of a sample, obtained from the rectal tumor, is measured in the presence and in the absence of said medicament, radiotherapy and/or chemotherapy and wherein said kinase activity in the presence said medicament, radiotherapy and/or chemotherapy is compared to the kinase activity in the absence of said medicament, radiotherapy and/or chemotherapy thereby determining the response of said patient to said medicament, radiotherapy and/or chemotherapy, wherein said kinase activity measurement provides phosphorylation profiles of said sample in the presence and in the absence of said medicament, radiotherapy and/or chemotherapy.

The measurement of the kinase activity of said sample preferably occurs by contacting said sample with at least one protein kinase substrate in the presence and in the absence of said medicament, radiotherapy and/or chemotherapy. Techniques from the prior art often require the incubation and/or pretreatment of the cells or tissues with said medicaments, radiotherapy and/or chemotherapy, preferably in vivo, during the culturing of the cells or tissues or during a large time period prior to the actual measurement of the kinase activity. The present invention provides that the medicament, radiotherapy and/or chemotherapy is added to the sample (or the sample is exposed to it) only just prior to contacting the sample with the protein kinase substrates and performing the kinase activity assay. Consequently, the present invention provides an in vitro primary screening tool which allows the use of a single sample which is split into a first part that is used for the incubation of the sample in the absence of a medicament, radiotherapy and/or chemotherapy while a second part of the sample is used for the incubation of the sample in the presence of a medicament, or exposed to radiotherapy and/or chemotherapy.

The present invention further relates in yet another embodiment to a method for determining or predicting the response of a patient diagnosed with rectal cancer to chemoradiotherapy, comprising the steps of:
(a) measuring the kinase activity of a sample, obtained from the rectal cancer tumor from said patient, thereby providing the phosphorylation levels of phosphorylation sites present in at least two of the peptide markers as listed in table 1; and,
(b) determining from said phosphorylation levels the response of said patient to chemoradiotherapy.

These and further aspects and embodiments are described in the following sections and in the claims.

BRIEF DESCRIPTION OF FIGURES

FIG. 1 provides, as depicted in the examples, a graphical representation showing the prediction of the response of a patient diagnosed with rectal cancer to chemoradiotherapy.

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the response of a patient diagnosed with rectal cancer to chemoradiotherapy by measuring kinase activity of a rectal cancer sample. The present invention further shows how the method and devices can be used to predict the response of patients diagnosed with rectal cancer to specific medicaments, radiotherapy and/or chemotherapy. The method of the present invention therefore adds to the existing assays currently used to select therapies in rectal cancer patients.

Preferably, in one embodiment of the present invention, methods are provided wherein the kinase activity is protein kinase activity. For purposes of the present invention, and as used herein the term "enzyme activity", "kinase activity" or "protein kinase activity" refer to the formation of reaction product(s) by a certain amount of enzyme, kinase or protein kinase acting on a substrate during the course of the assay.

Protein kinase activity is referred to as the activity of protein kinases. A protein kinase is a generic name for all enzymes that transfer a phosphate to a protein. About three to four percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by chemically adding phosphate groups to them. This process or activity is also referred to as phosphorylation.

Phosphorylation can therefore be regarded as the process of the addition of a phosphate group to a substrate. Phosphorylation usually results in a functional change of the substrate by changing enzyme activity, cellular location, or association with other proteins. Up to 30% of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine. The protein kinase activity monitored with the method of the present invention is preferably directed to protein kinases acting towards serine, threonine and/or tyrosine, preferably acting on both serine and threonine, on tyrosine or on serine, threonine and tyrosine and more preferably the method of the present invention if preferably directed to protein kinases acting towards tyrosines.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated kinase activity is a frequent cause of disease, particularly cancer, where kinases regulate many aspects that control cell growth, movement and death. Therefore monitoring the protein kinase activity in tissues can be of great importance and a large amount of information can be obtained when comparing the kinase activity of different tissue samples.

As described in the present invention, the inventors have surprisingly found that the response of a patient diagnosed with rectal cancer to chemoradiotherapy or neoadjuvant chemoradiotherapy can be predicted and/or determined on the basis of the measurement of the kinase activity of a rectal tumor sample.

The measurement of the kinase activity is performed by contacting a rectal tumor sample with one or more substrates, preferably protein kinase substrates, thereby generating a phosphorylation profile.

Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, during the measurement method the kinase enzymes present in the sample will phosphorylate, preferably one or more, of the phosphorylation sites on one or more protein kinase substrates. The inventors have observed essential differences between the kinase activity of rectal tumors having a different response to radiation therapy. Consequently, the inventors have observed that the kinases present in a rectal tumor sample will phosphorylate protein kinase substrates differently depending on the response to radiation of said rectal tumors.

The present invention therefore provides a method for determining or predicting the response of a patient diagnosed with rectal cancer to chemoradiotherapy. In a first embodiment of the present invention, the method comprises the steps of:

(a) measuring kinase activity of a sample, obtained from the rectal cancer tumor from said patient, thereby providing a phosphorylation profile of said sample, said phosphorylation profile comprising the phosphorylation levels of phosphorylation sites present in at least two peptide markers as listed in Table 1; and, (b) determining or predicting from said phosphorylation profile the response of said patient to chemoradiotherapy.

Preferably phosphorylation levels will be studied of phosphorylation sites present in at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or 86 of the peptide markers listed in Table 1.

In a preferred embodiment of the present invention, said chemoradiotherapy is preoperative chemoradiotherapy. The combination of radiotherapy and chemotherapy, called chemoradiotherapy, is advocated primarily because of the independent effect of each treatment modality. Chemotherapeutics may enhance radiocytotoxicity by means of increasing the initial DNA damage, inhibiting DNA repair, or slowing down cellular repopulation during fractionated radiotherapy. Radiotherapy and chemotherapy often target different phases of the cell cycle, and radiosensitization may in part be dependent on cell cycle synchronization of the tumor cell population.

As referred to in the present application rectal cancer regards a malignant cancerous growth in the tissues of the rectum. Cancer is a disease in which abnormal cells grow in an uncontrolled way. The World Health Organization (WHO) classifies tumors of the colon and rectum as epithelial tumors and nonepithelial tumors. The epithelial tumor class consists of adenoma tumors, intraepithelial neoplasia associated with chronic inflammatory diseases, carcinoma, carcinoid and mixed carcinoma-adenocarcinoma. The nonepithelial tumors consist of tumors including malignant lymphomas. Adenocarcinomas account for the vast majority of rectal cancers.

As used in the present invention, the term "sample" refers to a sample obtained from an organism (patient) such as human or from components (e.g. tissue or cells) of such an organism. Said sample is preferably obtained from a patient diagnosed with rectal cancer and needs to be derived from the tumor tissue of said patient. More preferably said sample is a rectal tumor tissue biopsy, fine needle biopsy, fine needle aspiration biopsy, core needle biopsy, open surgical biopsy or material from resected tumor. Said sample is thereby referred to as a 'clinical sample' which is a sample derived from a rectal cancer patient.

Said tumor tissue sample is preferably a fresh or a fresh frozen sample.

More preferably, said sample refers to a cell lysate of a rectal tumor tissue obtained through tumor tissue biopsy, fine needle biopsy, fine needle aspiration biopsy, core needle biopsy or an endoscopic biopsy. Alternatively said sample may be obtained from specific rectal tumor cell lines and in particular cell lysates thereof.

Alternatively said sample may be derived from a tumor sample that has been cultured in vitro for a limited period of time.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

As used in the present invention, the term "phosphorylation profile" refers to a data set representative for the phosphorylation levels of, preferably one or more, phosphorylation sites present on the protein kinase substrates. When measuring the kinase activity of a sample by contacting said sample with protein kinase substrates a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a protein kinase inhibitor. More frequently phosphorylation profiles of a sample will be measured using several protein kinase substrates in the same or sequentially carried out experiments. Preferably, the present invention determines tyrosine kinase activity levels or profiles.

It should be noted that a person skilled in the art will appreciate that the methods of the present invention can use phosphorylation profiles as a basis for determining or predicting the response of a patient diagnosed with rectal cancer to chemoradiotherapy. However, the phosphorylation levels of individual protein kinase substrates can also be used as a basis for determining or predicting the response of a patient diagnosed with rectal cancer to chemoradiotherapy.

It should be noted that for the measurement of the protein kinase activity, ATP, or any other phosphate source, needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a molecule capable of binding to the phosphorylated substrates. This binding can be detected by e.g. surface plasmon resonance or by the molecule being detectably labelled. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SYBR Green I & II [Molecular Probes], and the like), radiolabels (e.g. 3H, 125I, 35S, 14C, or 32P), enzymes (e.g. hydrolases, particularly phosphatases such as alkaline phosphatase, esterases and glycosidases, or oxidoreductases, particularly peroxidases such as horse radish peroxidase, and the like), substrates, cofactors, inhibitors, chemilluminescent groups, chromogenic agents, and colorimetric labels such as colloidal gold or coloured glass or plastic (e.g. polystyrene, polypropylene, latex, etc.), protein particles or beads.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the protein kinase substrates.

As used herein the term "chemoradiotherapy" refers to a method wherein high energy rays are used to kill cancer cells. It is a well established technique that is often used to treat cancer that started at the rectum. In many cases, chemoradiotherapy is given before surgery (preoperative chemoradiotherapy) for rectal cancer to shrink the tumor and prevent return of the cancer in that area.

The inventors have found that measuring the kinase activity of a rectal tumor sample, enables a differentiation between patients which will respond to chemoradiotherapy and non-responders. Compared to existing immunohistochemical and genetic methods, the methods of the present invention have been found more predictive. This surprising effect is due to the fact that the measurement method according to the present invention is directed towards the signalling pathways of the cancer cells thereby providing insight into the intrinsic biology of the individual tumors and their response to chemoradiotherapy and thus provide a more accurate determination of the response of a rectal tumor to neoadjuvant chemoradiotherapy.

The statistical analysis of the phosphorylation profiles and levels can be done using multivariate and/or univariate statistical methods known in the art.

In addition, because the phosphorylation profile is generated by comparing the phosphorylation levels of a number of protein kinase substrates, the phosphorylation profile is surprisingly found to be less affected by variation, for example biological variation, experimental variation, compared to other types of profiles. This provides a more robust, more sensitive, more reproducible and more reliable method for determining the response of a rectal tumor to chemoradiotherapy.

The inventors have surprisingly found that kinase activity measurements of rectal tumor biopsy sample, taken from LARC patients prior to chemoradiotherapy, enable to predict preoperatively the response of LARC to chemoradiotherapy. This prediction provides information on the efficacy of the preoperative chemoradiotherapy treatment.

The term "peptide markers" in the context of the present invention refers to the fact that the peptides as listed in Table 1 can be preferably used according to the methods of the present invention as target regions to measure the phosphorylation levels of phosphorylation sites of said markers in the presence of protein kinase present in samples. The phosphorylation levels of the individual phosphorylation sites present in said markers may be measured and compared in different ways. Therefore the present invention is not limited to the use of peptides identical to any of these peptide markers as listed in Table 1 as such. The skilled person may easily on the basis of the peptide markers listed in Table 1 design variant peptides compared to the specific peptides in said Table and use such variant peptides in a method for measuring phosphorylation levels of phosphorylation sites common to said peptide markers as listed in Table 1. These variant peptides may have one or more (2, 3, 4, 5, 6, 7, etc.) amino acids more or less than the given peptides and may also have amino acid substitutions (preferably conservative amino acid substitutions) as long as these variant peptides retain at least, preferably one or more, of the phosphorylation sites of said original peptides as listed in said table. Further the skilled person may also easily carry out the methods according to the present invention by using proteins (full length or N- or C-terminally truncated) comprising the amino acid regions of the "peptide markers" listed in Table 1 as sources for studying the phosphorylation of sites present in the amino acid regions of the peptides listed in Table 1. Also the skilled person may used peptide mimetics.

The protein kinase substrates as used in the methods described herein, are meant to include peptides, proteins or peptide mimetics comprising, preferably one or more, of the phosphorylation sites of the peptide markers of Table 1. Said, preferably one or more, phosphorylation sites are specifically phosphorylated by the protein kinases present in the sample thereby providing a phosphorylation profile. More preferably the protein kinase substrates (peptides, proteins or peptide mimetics) as used in the method of the present invention comprise, preferably one or more, of the phosphorylation sites present in at least two peptide markers as listed in Table 1. More particularly said protein kinase substrates represent the, preferably one or more, phosphorylation sites present in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or 86 peptide markers as listed in Table 1. In a more preferred embodiment the protein kinase substrates comprise or consist of, preferably one or more, phosphorylation sites present in all of the peptide markers listed in Table 1.

A person skilled in the art will appreciate that the phosphorylation sites present in a single peptide marker as listed in Table 1 enable determining or predicting the response of a patient diagnosed with rectal cancer to chemoradiotherapy or the response of said patient to treatment with a treatment including chemotherapy and radiation therapy. However, when the number of peptide markers as listed in Table 1 increases, so will increase the specificity and sensitivity of the method according to the present invention. When for example only one protein kinase substrate comprising the phosphorylation sites of a single peptide marker as listed in table 1 is used for determining or predicting the response of a patient diagnosed with rectal cancer to chemoradiotherapy, the accuracy of the method will be lower, compared to a method where the response prediction of rectal cancer to chemoradiotherapy uses multiple, such as for instance 20 or 25, protein kinase substrates comprising the phosphorylation sites of multiple peptide markers as listed in table 1. A high method accuracy will be obtained when all protein kinase substrates comprising the phosphorylation sites of all peptide markers as listed in table 1 and preferably SEQ ID NO 1 to 21 are used. More preferably, in a particular embodiment the method of the present invention SEQ ID NO 1, 2, 3, 4, 5, 6, 7, 21, 32, 42, 51, 54, 61, 62, 63, 67, 71, 74, 79, 80, 81, 82, 83, 85, 86 are used.

This subset has been constructed by assessing the error rate obtained with leave one out cross validation (LOOCV) of PLS-DA class prediction as a function of the number of included peptides. Included peptides were selected by training a PLS-DA classifier on the training set of each iteration of the LOOCV including all peptides, subsequently the n peptides with the highest absolute value of the regression coefficients were selected and a new classifier was trained based on these peptides, a prediction for the test sample was then obtained using the new classifier. On completion of the LOOCV the error rate was obtained as the percentage of samples that were incorrectly predicted. This procedure was repeated with the number of peptides n taking values in the range 5-86. The minimal error rate that was obtained included 25 peptides with SEQ ID NO 1, 2, 3, 4, 5, 6, 7, 21, 32, 42, 51, 54, 61, 62, 63, 67, 71, 74, 79, 80, 81, 82, 83, 85, 86. The results indicate that the 25 peptides can be used to provide the minimal error rate when classifying new samples.

Table 1: List of 86 peptide markers comprising phosphorylation sites used for determining the kinase activity, their sequence and SEQ ID NO The name of the peptide markers refers to the associated proteins and also refers to the start and the end position of the amino acid sequence.

| SEQ ID NO | Peptide marker Name | Peptide marker Sequence |
|---|---|---|
| 1 | PGFRB_572_584 | VSSDGHEYIYVDP |
| 2 | EGFR_1165_1177 | ISLDNPDYQQDFF |
| 3 | PGFRB_1014_1028 | PNEGDNDYIIPLPDP |
| 4 | MK07_211_223 | AEHQYFMTEYVAT |
| 5 | LAT_249_261 | EEGAPDYENLQEL |
| 6 | ERBB4_1277_1289 | IVAENPEYLSEFS |
| 7 | EPHB1_771_783 | DDTSDPTYTSSLG |
| 8 | EPHA1_774_786 | LDDFDGTYETQGG |
| 9 | EPHA7_607_619 | TYIDPETYEDPNR |
| 10 | K2C6B_53_65 | GAGFGSRSLYGLG |
| 11 | P85A_600_612 | NENTEDQYSLVED |
| 12 | EPOR_419_431 | ASAASFEYTILDP |
| 13 | FGFR2_762_774 | TLTTNEEYLDLSQ |
| 14 | PAXI_24_36 | FLSEETPYSYPTG |
| 15 | ANXA1_14_26 | IENEEQEYVQTVK |
| 16 | FAK2_572_584 | RYIEDEDYYKASV |
| 17 | ERBB2_870_882 | LDIDETEYHADGG |
| 18 | SRC8_CHICK_476_488 | EYEPETVYEVAGA |
| 19 | EPHA2_765_777 | EDDPEATYTTSGG |
| 20 | PAXI_111_123 | VGEEEHVYSFPNK |
| 21 | Abl_artificial_kinase_substrate | EAIYAAPFAKKK |
| 22 | TNNT1_2_14 | SDTEEQEYEEEQP |
| 23 | CBL_693_705 | EGEEDTEYMTPSS |
| 24 | CDK2_8_20 | EKIGEGTYGVVYK |
| 25 | JAK1_1015_1027 | AIETDKEYYTVKD |
| 26 | INSR_992_1004 | YASSNPEYLSASD |
| 27 | LAT_194_206 | MESIDDYVNVPES |
| 28 | EGFR_1103_1115 | GSVQNPVYHNQPL |
| 29 | CTNB1_79_91 | VADIDGQYAMTRA |
| 30 | PDPK1_369_381 | DEDCYGNYDNLLS |
| 31 | ERBB2_1241_1253 | PTAENPEYLGLDV |
| 32 | 41_654_666 | LDGENIYIRHSNL |
| 33 | EPOR_361_373 | SEHAQDTYLVLDK |
| 34 | FER_707_719 | RQEDGGVYSSSGL |
| 35 | RET_1022_1034 | TPSDSLIYDDGLS |
| 36 | FES_706_718 | REEADGVYAASGG |
| 37 | VGFR2_1052_1064 | DIYKDPDYVRKGD |
| 38 | SRC8_CHICK_470_482 | VSQREAEYEPETV |
| 39 | PDPK1_2_14 | ARTTSQLYDAVPI |
| 40 | JAK2_563_577 | VRREVGDYGQLHETE |
| 41 | PECA1_706_718 | KKDTETVYSEVRK |
| 42 | MBP_198_210 | ARTAHYGSLPQKS |
| 43 | VGFR2_989_1001 | EEAPEDLYKDFLT |
| 44 | NTRK2_696_708 | GMSRDVYSTDYYR |
| 45 | MET_1227_1239 | RDMYDKEYYSVHN |
| 46 | ACHD_383_395 | YISKAEEYFLLKS |
| 47 | PRGR_786_798 | EQRMKESSFYSLC |
| 48 | CD3Z_116_128 | KDKMAEAYSEIGM |
| 49 | PLCG1_764_776 | IGTAEPDYGALYE |
| 50 | RASA1_453_465 | TVDGKEIYNTIRR |
| 51 | PGFRB_768_780 | SSNYMAPYDNYVP |
| 52 | FRK_380_392 | KVDNEDIYESRHE |
| 53 | DYR1A_312_324 | CQLGQRIYQYIQS |
| 54 | PGFRB_771_783 | YMAPYDNYVPSAP |
| 55 | FAK1_569_581 | RYMEDSTYYKASK |
| 56 | DCX_109_121 | GIVYAVSSDRFRS |
| 57 | PGFRB_709_721 | RPPSAELYSNALP |
| 58 | TEC_512_524 | RYFLDDQYTSSSG |
| 59 | VGFR2_1168_1180 | AQQDGKDYIVLPI |
| 60 | MK12_178_190 | ADSEMTGYVVTRW |
| 61 | FGFR3_753_765 | TVTSTDEYLDLSA |
| 62 | PRRX2_202_214 | WTASSPYSTVPPY |
| 63 | SRC8_CHICK_492_504 | YQAEENTYDEYEN |

-continued

| SEQ ID NO | Peptide marker Name | Peptide marker Sequence |
|---|---|---|
| 64 | VGFR1_1326_1338 | DYNSVVLYSTPPI |
| 65 | ZAP70_485_497 | ALGADDSYYTARS |
| 66 | ODBA_340_352 | DDSSAYRSVDEVN |
| 67 | FGFR1_761_773 | TSNQEYLDLSMPL |
| 68 | PP2AB_297_309 | EPHVTRRTPDYFL |
| 69 | RAF1_332_344 | PRGQRDSSYYWEI |
| 70 | MK10_216_228 | TSFMMTPYVVTRY |
| 71 | AMPE_5_17 | EREGSKRYCIQTK |
| 72 | PGFRB_1002_1014 | LDTSSVLYTAVQP |
| 73 | RON_1346_1358 | SALLGDHYVQLPA |
| 74 | CDK7_157_169 | GLAKSFGSPNRAY |
| 75 | MK01_180_192 | HTGFLTEYVATRW |
| 76 | RB_804_816 | IYISPLKSPYKIS |
| 77 | VINC_815_827 | KSFLDSGYRILGA |
| 78 | MBP_259_271 | FGYGGRASDYKSA |
| 79 | PTN11_539_551 | SKRKGHEYTNIKY |
| 80 | CALM_95_107 | KDGNGYISAAELR |
| 81 | TYRO3_679_691 | KIYSGDYYRQGCA |
| 82 | ZBT16_621_633 | LRTHNGASPYQCT |
| 83 | MBP_263_275 | GRASDYKSAHKGF |
| 84 | NCF1_313_325 | QRSRKRLSQDAYR |
| 85 | NPT2A_501_513 | AKALGKRTAKYRW |
| 86 | VGFR2_944_956 | RFRQGKDYVGAIP |

It should further be noted that according to a preferred embodiment of the present invention the peptide markers as listed in Table 1 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80% and more preferably more than 90%.

In an alternative embodiment said protein kinase substrates represent the, preferably one or more, phosphorylation sites present in at least 1, 2, 3, 4, 5, 6, 7, 8, 9, 10, 11, 12, 13, 14, 15, 16, 17, 18, 19, 20 or 21 peptide markers with any of SEQ ID NO 1, 2, 3, 4, 5, 6, 7, 8, 9, 10, 11, 12, 13, 14, 15, 16, 17, 18, 19, 20 or 21.

In an alternative embodiment said protein kinase substrates represent the, preferably one or more, phosphorylation sites present in at least 1, 2, 3, 4, 5, 6, 7, 8, 9, 10, 11, 12, 13, 14, 15, 16, 17, 18, 19, 20, 21, 22, 23, 24 or 25 peptide markers with any of SEQ ID NO 1, 2, 3, 4, 5, 6, 7, 21, 32, 42, 51, 54, 61, 62, 63, 67, 71, 74, 79, 80, 81, 82, 83, 85, 86.

In yet another embodiment, the present invention relates to a method according to the present invention wherein step (b) is replaced by steps (c) and (d) as provided below. The method according to the present invention may therefore comprise the steps of:

(a) measuring kinase activity of a sample, obtained from the rectal cancer tumor from said patient, thereby providing a phosphorylation profile of said sample, said phosphorylation profile comprising the phosphorylation levels of phosphorylation sites present in at least two peptide markers as listed in Table 1;

(c) calculating a classifier parameter from said phosphorylation profile; and, (d) determining the response of said patient to chemoradiotherapy on the basis of said classifier parameter.

By establishing a classifier parameter for determining the response of a rectal cancer patient to chemoradiotherapy the method of the present invention establishes a criterion for analysing the results obtained from the method of the present invention. This criterion enables a person to provide a decision on the basis of a single or limited number of data. The person providing the decision does not have to interpret an entire set of data, but rather bases his conclusion on the basis of a single or limited number of criteria.

The term "classifier parameter" as used herein is a discriminating value which has been determined by establishing the phosphorylation profile of said sample. Said discriminating value determines the response of a rectal cancer patient to chemoradiotherapy. The classifier parameter includes information regarding the phosphorylation level of several protein kinase substrates. Classification is a procedure in which individual items are placed into groups based on quantitative information on one or more characteristics inherent in the items (e.g. phosphorylation levels or profiles of a sample) and based on a training set of previously labelled items (clinical response to chemoradiotherapy) A classifying parameter is calculated by applying a "classifier" to the measured phosphorylation levels of a sample. Based on the classifying parameter a sample is assigned to (or predicted to belong to) a class RCC or normal kidney tissue or in another embodiment of the present invention to instance RCC patient tissue responsive or non-responsive to one or more protein kinase inhibitors. The classifier has been previously determined by comparing samples which are known to belong to the respective relevant classes. For instance the classifier may be a mathematical function that uses information regarding the phosphorylation level of several protein kinase substrates which individual protein kinase substrates can be weighted based on the measured phosphorylation level of a number of protein kinase substrates (or values derived from that). Several methods are known in the art for developing a classifier including the neural network (Multi-layer Perceptron), support vector machines, k-nearest neighbours, Gaussian mixture model, naive bayes, decision tree, RBF classifiers, random forest, disciminant analysis, linear discriminant analysis, quadratic discriminant analysis, discriminant analysis-principal component analysis, partial least squares discriminant analysis, generalized distance regression and elastic net classification. The classifier parameter determined in this manner is valid for the same experimental setup in future individual tests.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to determine whether rectal cancer patient will respond to chemoradiotherapy, then the threshold value of the test can be changed which as a consequence will decrease the negative predictive value of the test to determine whether rectal cancer patient will not respond to chemoradiotherapy. If one wants to increase the negative predictive value of the test to determine whether rectal cancer patient will not respond to chemoradiotherapy, then the threshold value can be changed in the opposite direction which as a consequence will decrease the positive predictive value of the test to determine whether rectal cancer patient will respond to chemoradiotherapy.

It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the diagnostic engineers.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to determine whether rectal cancer patient will respond to chemoradiotherapy, then the threshold value of the test can be changed which as a consequence will decrease the negative predictive value of the test to predict whether the rectal cancer patient will not respond to chemoradiotherapy. If one wants to increase the negative predictive value of the test to predict whether a patient will not respond to chemoradiotherapy then the threshold value can be changed in the opposite direction which as a consequence will decrease the positive predictive value of patients responding to chemoradiotherapy.

It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by diagnostic engineers.

In yet another embodiment, the present invention relates to a method according to the present invention wherein said classifier parameter indicates said patient being a good responder to chemoradiotherapy if said classifier parameter is above a first predetermined threshold level, and wherein said classifier parameter indicates said patient being a poor responder to chemoradiotherapy if said classifier parameter is below a second predetermined threshold level.

In yet another embodiment, the present invention relates to a method according to the present invention wherein step (b) is replaced by steps (e) and (f) as provided below. The method according to the present invention may therefore comprise the steps of:

(a) measuring kinase activity of a sample, obtained from the rectal cancer tumor from said patient, thereby providing a phosphorylation profile of said sample, said phosphorylation profile comprising the phosphorylation levels of phosphorylation sites present in at least two peptide markers as listed in Table 1;

(e) comparing said phosphorylation profile to a first and a second reference phosphorylation profile; said first reference phosphorylation profile being representative for a good responder to chemoradiotherapy and said second reference phosphorylation profile being representative for a poor responder to chemoradiotherapy; and, (f) determining response of said patient to chemoradiotherapy on the basis of the comparison of said phosphorylation profile with said first and said second reference phosphorylation profile.

The poor responder to chemoradiotherapy as used herein correlates with a tumor which after resection and histochemical analysis using a Tumor Regression Grade (TRG) classifies as a score 4 or 5. A good responder to chemoradiotherapy correlates to a tumor which after resection has a Tumor Regression Grade (TRG) of 1, 2 or 3. The TRG is based on a 5-point scoring system and is determined on the surgically resected tumor specimens following completed chemoradiotherapy. TRG 1 and 2 means complete or close to complete response of the chemoradiotherapy and TRG 3 represent partial response, which all are responses in accordance with the intention of the preoperative therapy, which is tumor shrinkage (down-staging) to allow complete surgical removal with curation. In contrast, TRG 4 and 5 are considered non-responders, which means that the chemoradiotherapy has not worked and that chemoradiotherapy should not have been provided to these patients.

As used herein, a "reference phosphorylation profile" refers to a profile obtained through measuring the phosphorylation levels of protein kinase substrates. More specifically, a phosphorylation profile being representative for a good responder to chemoradiotherapy as used herein, refers to a reference phosphorylation profile wherein the phosphorylation levels of a set of protein kinase substrates are representative for a rectal tumor having a good response to chemoradiotherapy. Additionally, a phosphorylation profile being representative for a poor responder to chemoradiotherapy as used herein, refers to a reference phosphorylation profile wherein the phosphorylation levels of a set of protein kinase substrates are representative for a rectal tumor having a poor response to chemoradiotherapy.

The tissue-specific template can further be defined as the error-weighted log ratio average of the phosphorylation difference for the group of protein kinase substrates able to determine the response of a rectal cancer patient to chemoradiotherapy.

According to another embodiment, the present invention relates to the method of the present invention wherein said phosphorylation profile or said classifier parameter indicates good response, poor response or undetermined or intermediate response of said patient to chemoradiotherapy.

As used in the present application the response of a rectal cancer patient to chemoradiotherapy is generally divided into two types, a good responder (responder) or a poor responder (non-responder) and additionally some of the rectal tumors may be undetermined or intermediate. Whereas a rectal cancer patient being determined as a good responder, said patient shows a good response of the rectal tumor to chemoradiotherapy, and preferably preoperative chemoradiotherapy, a rectal cancer patient being determined as a poor responder, said patient shows no or almost no response of the rectal tumor to chemoradiotherapy, and preferably preoperative chemoradiotherapy. Consequently said poor responder can preferably receive a different type of treatment. The method of the present invention specifically enables the distinction between rectal tumors responding and not responding to preoperative chemoradiotherapy. By predicting the response of rectal cancer patient to chemoradiotherapy one enables to provide more information regarding the best suited treatment of the patient.

In another embodiment, the present invention regards the method according to the present invention wherein said peptide markers are any of the peptide markers selected from the group consisting of the peptide markers with any of SEQ ID NO 1 to 21.

According to a particular embodiment, the present invention regards the method according to the present invention wherein said peptide markers are any of the peptide markers selected from the group consisting of the peptide markers with any of SEQ ID NO 1, 2, 3, 4, 5, 6, 7, 21, 32, 42, 51, 54, 61, 62, 63, 67, 71, 74, 79, 80, 81, 82, 83, 85, and 86.

More particularly said protein kinase substrates represent the, preferably one or more, phosphorylation sites present in at least 1, 2, 3, 4, 5, 6, 7, 8, 9, 10, 11, 12, 13, 14, 15, 16, 17, 18, 19, 20 or 21 peptide markers with any of SEQ ID NO 1 to 21. In a more preferred embodiment the protein kinase substrates comprise or consist of, preferably one or more, phosphorylation sites present in all of the peptide markers with any of SEQ ID NO 1 to 21.

As used herein, the term "protein kinase inhibitor" refers to a type of enzyme inhibitor which blocks the action of one or more protein kinases, hence they can be subdivided or characterised by peptides or proteins whose phosphorylation is inhibited. Examples of protein kinase inhibitors for use in the method of the present invention are Dasatinib (currently used for the treatment of leukaemia); erlotinib (currently used for the treatment of non-small cell lung cancer); gefitinib (currently used for the treatment of non-small cell lung cancer); imatinib (currently used for the treatment of gastrointestinal stromal tumors and leukaemia); lapatinib (currently used for the treatment of breast cancer); nilotinib (currently used for the treatment of leukaemia); sorafinib (currently used for the treatment of renal cell carcinoma and hepatocellular carcinoma; Sunitinib (currently used for the treatment of renal cell carcinoma); temsirolimus (currently used for the treatment of renal cell carcinoma); ABT-869; AEE788; Alvocidib; AP23464; AP23846; AP23848; ARRY-142886; ARRY-334543; AT-7519; Axitinib; AZD0530; AZD1152; BIBW-2992; BIRB-796; BMI-1026; BMS-599626; Bosutinib; Brivanib; Canertinib; CCT129202; Cediranib; CEP-7055; CP-547632; CP-724714; Dovitinib; E7080; Enzastaurin; everolimus; FI-700; Gossypol; HKI-272; HMN-176; HMN-214; INNO-406; JNJ-7706621; KRX-0601; LBW242; Lestaurtinib; Midostaurin; MK-0457; MLN8054; MP-470; Neratinib; ON0123380; ON01910; ON-01901; OSI-930; Pazopanib; PD166326; PD173955; PD180970; Pelitinib; PF-2341066; PHA665752; PHA-739358; PX-866; R-547; Seliciclib; Semapimod; Semaxanib; SNS-032; SU011248; SU014813; SU11248; SU11274; SU14813; Tandutinib; Telatinib; TSU-68; UCN-01; Vandetanib; Vatalanib; VE-465; ZM 447439 and protein kinase inhibitors used in research including Tyrphostin-1; Tyrphostin-23; Tyrphostin-51; Tyrphostin-63; AG-1007; AG-1112; AG-1433; RG-13022; SU-1498; I-OMe-Tyrphostin; AG-538; Protein Kinase G inhibitor peptide (Arg-Lys-Arg-Ala-Arg-Lys-Glu); Geldanamycin from Streptomyces hygroscopicus; Lavendustin A; and Genistein.

Additionally, the inventors have further found that by adding a protein kinase inhibitor in step (a) of the method of the present invention allows further differentiation between the obtained phosphorylation profiles. When using both a protein kinase inhibitor while measuring the kinase activity, two different phosphorylation profiles can be obtained: a phosphorylation profile in the absence of a protein kinase inhibitor and a phosphorylation profile in the presence of a protein kinase inhibitor. By providing two different phosphorylation profiles more information regarding the response of a rectal tumor to chemoradiotherapy can be obtained. Another embodiment of the present invention relates to a method according to the present invention wherein said kinase substrates carrying phosphorylation sites are located or immobilized on a solid support, and preferably a porous solid support. Preferably said immobilized kinase substrates carrying phosphorylation sites will be immobilized proteins, peptides or peptide mimetics.

In a preferred embodiment of the present invention peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which are covalently linked via peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences listed in Table 1. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

For measuring the kinase activity of the sample a large variety of methods and formats are known in the art. The kinase activity can for example be measured using ELISA and multiplex ELISA techniques, blotting methods, mass spectrometry, capillary electrophoresis, bead arrays, macroarrays, microarrays or any other method known in the art. Depending on the type of kinase activity measurement method the solid support on which the proteins, peptides or peptide mimetics are fixed may vary. Whereas in ELISA the protein kinase substrates are attached to the walls of the microtiterplates, in microarrays the protein kinase substrates are immobilized on and/or in the microarray substrate.

In a preferred embodiment of the present invention the protein kinase substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

In a further embodiment, the present invention relates to a method according to the present invention wherein said solid support (microarray) comprises any of the peptides as listed in Table 1 immobilized thereto.

In a further embodiment, the present invention relates to a method according to the present invention wherein said solid support (microarray) comprises each of the peptide as listed in Table 1 immobilized thereto.

In a further embodiment, the present invention relates to a method according to the present invention wherein said solid support (microarray) comprises any of the peptides with SEQ ID NO 1 to 21.

In a further embodiment, the present invention relates to a method according to the present invention wherein said solid support (microarray) comprises each of the peptides with SEQ ID NO 1 to 21 immobilized thereto.

In a further embodiment, the present invention relates to a method according to the present invention wherein said chemoradiotherapy is preoperative neoadjuvant chemoradiotherapy.

Another embodiment of the present invention regards a method for predicting the response of a patient, diagnosed with rectal cancer, to a medicament, radiotherapy and/or chemotherapy, wherein the kinase activity of a sample, obtained from the rectal tumor, is measured in the presence and in the absence of said medicament, radiotherapy and/or chemotherapy and wherein said kinase activity in the presence said medicament, radiotherapy and/or chemotherapy is compared to the kinase activity in the absence of said medicament, radiotherapy and/or chemotherapy thereby determining the response of said patient to said medicament, radiotherapy and/or chemotherapy, wherein said kinase activity measurement provides phosphorylation profiles of said sample in the presence and in the absence of said medicament, radiotherapy and/or chemotherapy.

By measuring the kinase activity of a sample, obtained from the rectal tumor from said patient, in the presence and in the absence of a medicament, radiotherapy and/or chemotherapy, the effect of that medicament, radiotherapy and/or chemotherapy to the rectal tumor can be assessed. This method was found particularly useful in the prediction of response to said medicament, radiotherapy and/or chemotherapy, and to enable the distinction between responders and non-responders in the treatment with said medicament, radiotherapy and/or chemotherapy.

It should be noted that the observed response of the patient to said medicament, radiotherapy and/or chemotherapy can either be a positive response, wherein the medicament, radiotherapy and/or chemotherapy will improve the treatment of said patient, or a negative response, wherein the medicament, radiotherapy and/or chemotherapy has a negative or no influence on the treatment of said patient.

The medicament as used in the method of the present invention can be any kind of chemical substance for instance used in the treatment, cure, prevention, or diagnosis of disease or used to otherwise enhance physical or mental well-being. Specifically said medicament can be a kinase inhibitor, and more preferably a protein kinase inhibitor and most preferably a small molecule protein kinase inhibitor.

The chemotherapy as used in the method of the present invention refers to any kind of treatment of disease by chemicals that kill cells, both good and bad, but specifically cancer cells. Chemotherapy acts by killing cells that divide rapidly, one of the main properties of cancer cells. Most commonly antineoplastic drugs are used to treat cancer.

The radiotherapy as used in the method of the present invention refers to the medical use of ionizing radiation as part of cancer treatment to control malignant cells. Radiotherapy is a technique commonly known in the art and may be used for curative or adjuvant or neoadjuvant cancer treatment.

In another embodiment of the present invention the method for determining or predicting the response of a patient diagnosed with rectal cancer to chemoradiotherapy, uses phosphorylation profiles which comprise the phosphorylation levels of the phosphorylation sites, and preferably one or more phosphorylation sites, present in any of the peptide markers as listed in Table 1.

Preferably also this method will use two or more of said peptide markers as described above. More preferably this method uses, preferably one or more, phosphorylation sites present in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or 86 peptide markers as listed in Table 1.

Also for this embodiment, the amount and the type of peptides, proteins or peptide mimetics to be used is as described above. Phosphorylation levels can also be measured according to the invention, without the necessity to generate phosphorylation profiles thereof.

It is clear that effects of a medicament, radiotherapy and/or chemotherapy or a treatment thereof can be monitored using this method. The medicament, radiotherapy and/or chemotherapy or a treatment thereof affects the degree of inhibition, the potency and/or the selectivity of the kinases in the sample. More peptide inhibition is caused by the larger effect of the medicament, radiotherapy and/or chemotherapy or treatment thereof on the kinases in the sample and therefore the drug is less selective. Also an increased peptide inhibition would lead to a larger amount of normal tissues being affected by the drug, making the drug less tumor tissue specific.

The present invention also relates according to another embodiment to an array for carrying out the methods of the present invention, said array comprising immobilized proteins, peptides or peptide mimetics comprising, preferably one or more, phosphorylation sites present in any of the peptide markers as listed in table 1. More preferably said array comprises immobilized proteins, peptides or peptide mimetics comprising, preferably one or more, phosphorylation sites present in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or 86 peptide markers as listed in Table 1.

More preferably said array comprises immobilized proteins, peptides or peptide mimetics comprising, preferably one or more, phosphorylation sites present in at least 1, 2, 3, 4, 5, 6, 7, 8, 9, 10, 11, 12, 13, 14, 15, 16, 17, 18, 19, 20 or 21 peptide markers with SEQ ID NO 1 to 21.

In an alternative embodiment said said array comprises immobilized proteins, peptides or peptide mimetics comprising, preferably one or more, phosphorylation sites present in at least 1, 2, 3, 4, 5, 6, 7, 8, 9, 10, 11, 12, 13, 14, 15, 16, 17, 18, 19, 20, 21, 22, 23, 24 or 25 peptide markers with any of SEQ ID NO 1, 2, 3, 4, 5, 6, 7, 21, 32, 42, 51, 54, 61, 62, 63, 67, 71, 74, 79, 80, 81, 82, 83, 85, 86.

Said proteins, peptides or peptide mimetics are preferably at least 25% of proteins, peptides or peptide mimetics on said array. Said arrays may further comprise one or more immobilized proteins, peptides or peptide mimetics which are used as calibration means for performing the methods according to the present invention.

More particularly said array comprises immobilized proteins, peptides or peptide mimetics comprising, preferably one or more, phosphorylation sites as described in detail above representing the peptide markers as listed in table 1. Additionally said proteins, peptides or peptide mimetics are preferably at least 25%, at least 50%, at least 70%, at least 80%, at least 90% or 100% of the proteins, peptides or peptide mimetics on said array.

The type of arrays, to be used according to this embodiment, are known in the art and are further detailed above.

The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method according to the present invention.

The present invention further relates to a computer system comprising a processor, and a memory coupled to said processor and encoding one or more programs, wherein said one or more programs instruct the processor to carry out a method according to the present invention.

The present invention also relates in another embodiment to a kit for determining or predicting the response of a patient diagnosed with rectal cancer to chemoradiotherapy, comprising at least one array according to the present invention, and optionally a computer readable medium having recorded thereon one or more programs for carrying out the method according to the present invention.

The present invention further relates in yet another embodiment to a method for determining or predicting the response of a patient diagnosed with rectal cancer to chemoradiotherapy, comprising the steps of:

(a) measuring the kinase activity of a sample, obtained from the rectal cancer tumor from said patient, thereby providing the phosphorylation levels of phosphorylation sites present in at least two of the peptide markers as listed in table 1; and, (b) determining from said phosphorylation levels the response of said patient to chemoradiotherapy.

Since the present inventors have identified a surprisingly useful set of peptide markers to be used in methods for determining or predicting the response of a patient diagnosed with rectal cancer to chemoradiotherapy, the skilled man may carry out any method as defined above wherein he measures the kinase activity of any of the peptide markers of Table 1. Also this method may be carried out using the amount and type of peptides, proteins or protein mimetics as defined above. The formats for carrying out these methods are also as for the methods described above.

The present invention is hereafter exemplified by the illustration of particular, non-limiting examples.

EXAMPLES

Example 1

Example Showing how Responders and Non-Responders to Chemoradiotherapy can be Distinguished According to a Phosphorylation Profile LARC patients were recruited in a clinical trial as further described under ClinicalTrials.gov Identifier, NCT00278694. The purpose of this Phase II clinical trial was to determine the efficacy of oxaliplatin and 5-fluorouracil (capecetabine) based preoperative chemoradiotherapy in rectal cancer patients. This preoperative chemoradiotherapy is emerging as the gold standard for treatment of locally advanced rectal cancer. In this clinical trial preoperative chemoradiotherapy intends to achieve tumor down-staging to allow subsequent radical resection. However, chemoradiotherapy results in substantial variation of responses within the patient population and may cause short-term and long-term complications. Patients were treated with chemoradiotherapy using radiotherapy of 50 Gy in 2-Gy fractions 5 days per week for a period of 5 weeks, chemotherapy consisting of capecitabine 825 mg/m$^2$ twice daily on radiotherapy days and oxaliplatin 50 mg/m$^2$ once weekly.

The response to the chemoradiotherapy was tested based on histopathological tumor response using the validated Tumor Regression Grade (TRG) scoring model. The TRG is based on a 5-point scoring system and is determined on the surgically resected tumor specimens following completed chemoradiotherapy. TRG 1 and 2 means complete or close to complete response of the chemoradiotherapy and TRG 3 represent partial response, which all are responses in accordance with the intention of the preoperative therapy, which is tumor shrinkage (down-staging) to allow complete surgical removal with curation. In contrast, TRG 4 and 5 is considered non-responders, which means that the chemoradiotherapy has not worked and that chemoradiotherapy should not have been provided to these patients.

The contents of tumor cells for 19 patient biopsies were in the range of 20% to 70%, based on HE staining. 5 biopsies were from patients that achieved TRG-1 (complete response), 7 biopsies were from patients that achieved TRG-2 (good response), and 7 biopsies were from patients without response of the preoperative chemoradiotherapy (TRG-4; non-responders).

Tumor tissue biopsies were sectioned in 10 µm thick slices to a total volume of about 1.4 to 2.4 mm$^3$, then lysed in 36 microliter per mm$^3$ tumor tissue Mammalian Extraction Buffer (M-PER) containing phosphatase and protease inhibitors. Five microliter of the lysis solution was pipetted into a reaction mixture composed of 1×ABL buffer (10×Abl buffer (New England Biolabs, cat.nr B6050S-100 mM MgCl2, 10 mM EGTA, 20 mM DTT and 0.1% Brij 35 in 500 mM Tris/HCl, pH 7.5), 0.1% Bovine Serum Albumin, 100 µM ATP, 20 µg/ml phosphotyrosine antibody to an end volume of 40 microliter. Before incubation of the lysate reaction mixtures on the PamChip substrate array a blocking step was carried out on the substrate arrays with 2% bovine serum albumin. After loading of the lysate reaction mixtures into substrate arrays comprising 140 protein protein kinase substrates, including the 86 protein kinase peptide substrates as listed in Table 1, incubation was commenced thereby measuring the kinase activity of the sample. Each tumor tissue lysates was tested in four technical replicates on the substrate arrays. In total 3 times 96 substrate arrays were used. During 30 cycles of pumping the lysate reaction mixture through the array, peptide phosphorylation was detected by an antibody present in the lysate reaction mixture. Real time data were obtained by measuring fluorescence of the bound anti-phosphotyrosine antibody after each 5 cycles. Images of the array were taken during the incubation of the array and after 30 cycles of incubation. After 30 cycles of incubation and imaging, the antibody mixture was removed and the array was washed. Images were collected at different exposure times.

Signals for each spot on the image were quantified. Image quantification and data processing was conducted with dedicated PamGene software (Evolve and Bionavigator).

Subsequent data analysis was performed using Matlab (release 2007B, MathWorks Inc), wherein the obtained signals were normalized and correlated. A 1-way ANOVA analysis provided 21 peptides (SEQ ID NO 1 to 21) which showed a significant (p<0.05) difference over TRG.

Furthermore a prediction to chemoradiotherapy was performed with the 86 peptides as enlisted in Table 1. Partial Least Squares Discriminant Analysis (PLS-DA) was used as classifier.

The PLS-DA class prediction resulted are shown in FIG. 1. The FIGURE shows that only one out or seven non-responder samples were misclassified and twelve out of twelve responders were correctly classified.

FIG. 1 shows on the Y-axis the prediction obtained for 19 of the rectal tumor biopsy samples that were used to build a mathematical classifier to distinguish good-responders (TRG 1 and 2) from poor-responders (TRG 4). The samples are sorted along the X-axis. Samples from good-responders, TRG score 1 and 2, are represented by a black symbol, whereas non-responder samples, TRG score 4, are represented by a grey symbol. Samples are classified as responders if the prediction <0 and as non-responders if the prediction >0. Only one non-responder sample was misclassified as a responder sample.

The invention claimed is:

1. A method for predicting the response of a patient diagnosed with rectal cancer to chemoradiotherapy, comprising the steps of: (a) measuring tyrosine kinase activity of a sample, obtained from the rectal cancer tumor from said patient, thereby providing the phosphorylation levels of tyrosine kinase phosphorylation sites present in at least 25 of the peptide markers of SEQ ID NOs: 1-86; and, (b) determining from said phosphorylation levels the response of said patient to chemoradiotherapy.

2. A method for predicting the response of a patient diagnosed with locally advanced rectal cancer to chemoradiotherapy, comprising the steps of: (a) measuring tyrosine kinase activity of a sample, obtained from the rectal cancer tumor from said patient, thereby providing a phosphorylation profile of said sample, said phosphorylation profile comprising the phosphorylation levels of tyrosine kinase phosphorylation sites present in at least 25 of the peptide markers of SEQ ID NOs: 1-86; and, (b) determining from said phosphorylation profile the response of said patient to chemoradiotherapy.

3. The method according to claim 2, wherein step (b) comprises a step of calculating a classifier parameter from said phosphorylation profile; and a step of determining the response of said patient to chemoradiotherapy on the basis of said classifier parameter.

4. The method according to claim 3, wherein said classifier parameter indicates said patient being a good responder to chemoradiotherapy if said classifier parameter is above a first predetermined threshold level, and wherein said classifier parameter indicates said patient being a poor responder to chemoradiotherapy if said classifier parameter is below a second predetermined threshold level.

5. The method according to claim 2, wherein step (b) comprises a step of comparing said phosphorylation profile to a first and a second reference phosphorylation profile; said first reference phosphorylation profile being representative for a good responder to chemoradiotherapy and said second reference phosphorylation profile being representative for a poor responder to chemoradiotherapy; and a step of determining the response of said patient to chemoradiotherapy on the basis of the comparison of said phosphorylation profile with said first and said second reference phosphorylation profile.

6. The method according to claim 2, wherein said phosphorylation profile indicates good response, poor response or undetermined response of said patient to chemoradiotherapy.

7. The method according to claim 1, wherein said phosphorylation sites are present on proteins, peptides or peptide mimetics immobilized on a solid support.

8. The method according to claim 7, wherein said peptides are at least two peptides from SEQ ID NOs: 1-86.

9. The method according to claim 7, wherein said peptides are at least SEQ ID NOs: 1 to 21.

10. The method according to claim 7, wherein the solid support is a porous solid support.

11. The method according to claim 1, wherein said chemoradiotherapy is preoperative neoadjuvant chemoradiotherapy.

12. A computer program product for use in conjunction with a computer having a processor and a memory connected to the processor, said computer program product comprising a non-transitory computer readable storage medium having a computer program mechanism encoded thereon, wherein said computer program mechanism may be loaded into the memory of said computer and cause said computer to carry out the method of claim 2.

* * * * *